(12) United States Patent
Bohus et al.

(10) Patent No.: US 8,282,950 B2
(45) Date of Patent: Oct. 9, 2012

(54) MICROEMULSIONS AND THEIR USE FOR IMPROVING THE BIOLOGICAL EFFICACY OF PESTICIDES

(75) Inventors: Peter Bohus, Caronno Varesino (IT); Gianfranco Paganini, Magnago (IT); Giuseppe Li Bassi, Gavirate (IT)

(73) Assignee: Lamberti SpA, Albizzate (VA) (IT)

( * ) Notice: Subject to any disclaimer, the term of this patent is extended or adjusted under 35 U.S.C. 154(b) by 300 days.

(21) Appl. No.: 12/601,765

(22) PCT Filed: Oct. 25, 2007

(86) PCT No.: PCT/EP2007/009270
§ 371 (c)(1),
(2), (4) Date: Nov. 24, 2009

(87) PCT Pub. No.: WO2008/019891
PCT Pub. Date: Feb. 21, 2008

(65) Prior Publication Data
US 2010/0173782 A1     Jul. 8, 2010

(30) Foreign Application Priority Data
May 24, 2007 (IT) .................................. VA07A0047

(51) Int. Cl.
*A01N 25/00* (2006.01)
(52) U.S. Cl. ..................................... 424/405; 504/116.1
(58) Field of Classification Search ........................ None
See application file for complete search history.

(56) References Cited

U.S. PATENT DOCUMENTS 6,255,253 B1 * 7/2001 Foerster et al. ............... 504/363

FOREIGN PATENT DOCUMENTS

| EP | 392127 | * | 6/1889 |
| EP | 729700 | * | 9/1996 |
| WO | WO 0069261 | * | 11/2000 |
| WO | WO 2004080177 | * | 9/2004 |

* cited by examiner

*Primary Examiner* — Alton Pryor
(74) *Attorney, Agent, or Firm* — Mossman, Kumar & Tyler PC

(57) ABSTRACT

Homogenous and stable adjuvants in the form of microemulsions for use in agriculture containing: a) a mixture of surfactants comprising i) one or more anionic derivatives of an alkylpolyglycoside; ii) one or more alkylpolyglycosides; iii) one or more anionic derivatives of a fatty alcohol; b) one or more methyl esters of fatty acids deriving from the transesterification of vegetable oils, one or more vegetable oils, or mixture thereof; c) one or more nonionic surfactants; d) water.

20 Claims, No Drawings

MICROEMULSIONS AND THEIR USE FOR IMPROVING THE BIOLOGICAL EFFICACY OF PESTICIDES

TECHNICAL FIELD

The present invention relates to homogenous and stable adjuvants in the form of microemulsions for use in agriculture, for example as a tank-mix additive of postemergence herbicides and/or foliar treatment fungicides applied as an aqueous spray.

The components of the adjuvants of the present invention act synergistically at low dosage to increase spray retention, and they provide lipophilic and hydrophilic environments in the spray deposits, enhancing leaf penetration and efficacy of herbicides and/or fungicides.

The adjuvants of the present invention are provided as single stable formulations and reduce the need to add separate components to a spray tank mix.

BACKGROUND ART

Large amount of mineral and vegetable oils are used as adjuvants in order to improve biological efficacy of fungicidal and/or herbicide formulations. These substances must be uniformly dispersed in aqueous spray to provide their homogeneous distribution onto the treated surface in the field. Therefore, they are usually formulated as emulsifiable concentrate or eventually as concentrated macroemulsion and diluted with water short before application.

In the case of mineral oils the classical and traditional formulation comprises nonylphenol ethoxylates as emulsifiers.

Fatty alcohol ethoxylates are also used as emulsifiers for these systems, as described for example in U.S. Pat. No. 4,966,728 (BASF).

There is currently high demand to replace mineral oil with vegetable oils since they are less phytotoxic, and have better ecotoxicological profile and environmental impact.

Transesterified triglycerides and vegetable oils are well known adjuvants and are normally used in aqueous spray in emulsified form, usually obtained from emulsifiable concentrate.

Also, numerous tank-mix adjuvant based on methyloleate are described in the form of emulsifiable liquid which upon dilution with water form kinetically stable oil-in-water macroemulsions.

Vegetable oils and/or methylated vegetable oils (transesterified triglycerides) require more sophisticated emulsifier system than mineral oils, particularly when fluid oil-in-water macroemulsions must be prepared.

Low viscous emulsifiable liquid which upon dilution with water form kinetically stable oil-in-water macroemulsions show main disadvantages, since often creamy or oily separation occurs and hence good homogenisation of the product is required before application.

Therefore it is highly desirable to obtain adjuvants based on vegetable oils and/or methylated vegetable oils in the form of fluid microemulsions.

Submicron droplets or microemulsion systems are described in adjuvants for pharmaceutical applications (for example in U.S. Pat. No. 6,451,325 and U.S. Pat. No. 6,299,884).

Microemulsions for agrochemical applications are also described in the patent literature.

U.S. Pat. No. 6,589,913 describes agrochemical glyphosate formulations which show microemulsion structure.

U.S. Pat. No. 5,905,072 describes microemulsions as adjuvants for systemic fungicides containing methyl esters of fatty acids, and specific mixtures of non-ionic and anionic surfactants.

The use of alkyl(oligo)glycosides in microemulsions comprising an oil phase and an agrochemical is described for example in U.S. Pat. No. 6,255,253.

The presence of various surfactants in microemulsions is known not only to influence the stability of the composition, but also to possibly enhance the biological activity of the agrochemical formulation.

It is known that, when a dilute aqueous composition of pesticide is applied to foliage by conventional hydraulic spraying, the presence of surfactants in the dilute aqueous composition can alter the size distribution of the spray droplets, typically increasing the percentage of spray volume in the form of small droplets and reducing the percentage of spray volume in the form of large droplets.

As smaller droplets have lower momentum than larger droplets, these smaller droplets are less likely to rebound from a foliar surface and consequently are more likely to be retained on that surface.

Spray retention can also be facilitated by adhesion between surfactant molecules in a spray droplet and the foliar surface, which in most plants is waxy and hydrophobic.

This adhesion reduces not only rebound but also run-off of spray droplets from the foliar surface.

Surfactants also tend to increase the area of contact between a spray droplet and a foliar surface, and in many cases enhance penetration of a systemic pesticide from the droplet into and through cuticles of leaves to reach internal leaf tissues.

The molecules of systemic pesticide compound must go through several barriers.

Among these, one of the most important is believed to be the lipophilic cuticle on the foliar surface to which the pesticide is applied.

It has therefore been theorised that it would be desirable to place the pesticide compound into an amphiphilic medium which would keep better compatibility between the lipophilic cuticle and the pesticide, and thereby facilitate penetration of pesticide into and through the cuticle.

Amphiphilic carrier can be easily built using surfactants.

Through these and perhaps other effects, amphiphilic materials including surfactants have long been known to increase the biological effectiveness of pesticide, and to act as adjuvants.

DISCLOSURE OF INVENTION

It has now been found that fatty acid esters obtained from transesterification of vegetable oils and vegetable oils can be formulated in the form of microemulsions, as stable transparent clear liquids, and with enhanced biological activity, when water and specific amounts and kinds of surfactants are co-formulated with them.

Accordingly, the present invention relates to adjuvants in the form of stable microemulsions containing: a) a mixture of surfactants comprising i) one or more anionic derivatives of an alkylpolyglycoside; ii) one or more alkylpolyglycosides; iii) one ore more anionic derivatives of a fatty alcohol; b) one or more methyl esters of fatty acids deriving from the transesterification of vegetable oils, one or more vegetable oils, or mixture thereof; c) one or more nonionic surfactant; d) water.

Preferably, the adjuvants of the invention contain: a) from 5 to 20% by weight of the mixture of surfactants, the mixture comprising from 30% to 60% by weight of anionic derivative of an alkylpolyglycoside, from 30% to 60% by weight of alkylpolyglycoside and from 5% to 20% by weight of anionic derivative of fatty alcohol, their balance being 100; b) from 20 to 40% by weight of methyl esters of fatty acids deriving from transesterification of vegetable oils or from 20 to 40% by weight of vegetable oils; c) from 25 to 35% by weight of nonionic surfactant; d) from 10 to 40% by weight of water.

Preferred nonionic surfactant are ethoxylated and/or propoxylated derivatives of linear or branched fatty alcohols having from 6 to 20 carbon atoms.

According to a preferred embodiment of the invention the adjuvants of the invention contain: a) from 5 to 20% by weight of a mixture of surfactants, the mixture comprising from 30% to 60% by weight of an anionic derivative of an alkylpolyglycoside, from 30% to 60% by weight of an alkylpolyglycoside and from 5% to 20% by weight of an anionic derivative of a fatty alcohol, their balance being 100; b) from 20 to 40% by weight of methyl esters of fatty acids deriving from transesterification of vegetable oils or from 20 to 40% by weight of vegetable oils; c) from 25 to 35% by weight of an ethoxylated and/or propoxylated derivatives of linear or branched fatty alcohols having from 6 to 20 carbon atoms; d) from 10 to 40% by weight of water.

Mixtures of surfactants utilisable as component a) are described in EP 1,179,979.

The alkylpolyglycosides of the mixture of surfactants are the aliphatic alkylpolyglycosides represented by the formula (I) R—O-(G)$_x$ where: R is a saturated or unsaturated aliphatic alkyl group having from 6 to 20 carbon atoms, linear or branched; O is an oxygen atom; G is a residue of a reducing saccharide connected to R—O by means of an ethereal O-glycosidical bond; x is a number from 1 to 10, representing the average degree of oligomerisation of G.

Preferably R is an alkyl group having from 8 to 16 atoms of carbon, G is a residue of a reducing saccharide and x is a number between 1 and 2.

The preferred alkylpolyglycosides according to the invention, are compounds of formula (I) in which G is a residue of glucose.

The compounds of formula (I) are known, as well as their methods of preparation, and are for instance described in U.S. Pat. No. 3,219,656, U.S. Pat. No. 3,547,828 and U.S. Pat. No. 3,839,318.

The preferred compounds of formula (I) reported above are commercially available products and are endowed with an high biodegradability.

The anionic derivatives of alkylpolyglycosides of the mixture of surfactants are compounds represented by the formula (II) [R'—O-(G)$_x$]$_n$-(D)$_y$, where: R' is a aliphatic alkyl group, saturated or unsaturated, linear or branched, having from 6 to 20 atoms of carbon, preferably from 8 to 16 atoms of carbon; G is a residue of a reducing saccharide, preferably of glucose, connected to R'—O by means of an ethereal O-glycosidical bond; O is an oxygen atom; D is an acyl residue connected to an oxygen atom of the residue G, and derived from a bicarboxylic acid or a polycarboxylic acid having an aliphatic chain from 2 to 8 carbon atoms, linear or branched, saturated or unsaturated, not substituted or substituted with one or more hydroxyl groups, and in which at least one carboxylic group is salified or in acid form; n is a number between 1 and m−1, where m is the number of carboxylic groups in the acid that originates D; x has the same meaning as described above for the compounds of formula (I); y is a number from 1 to 10 representing the degree of average esterification of (G)$_x$.

Preferred anionic derivatives of alkylpolyglycosides according to the present invention, are compounds of formula (II), in which R' is an alkyl group having from 8 to 16 atoms of carbon and D is the acyl residue of a carboxylic acid selected from the group consisting of citric acid, sulfosuccinic acid, tartaric acid, maleic acid and malic acid.

The above mentioned anionic derivatives of alkylpolyglycosides of formula (II) are known and they can be prepared as described, for example, in EP 258 814, or in EP 510 564.

The anionic derivatives of fatty alcohols of the mixture of surfactants are represented by the formula (III) R"—O-D' and they can be prepared by esterification of a carboxylic acid with fatty alcohols of formula R"—OH, where: R" is an aliphatic alkyl group, saturated or unsaturated, linear or branched, having from 6 to 20 atoms of carbon, preferably from 8 to 16 atoms of carbon; O is an oxygen atom; D' is an acyl residue of a bicarboxylic acid or of a polycarboxylic acid having an aliphatic chain with from 2 to 8 atoms of carbon, saturated or unsaturated, linear or branched, not substituted or substituted with one or more hydroxyl groups, and in which at least one carboxyl group is salified or in its acid form.

Preferred anionic derivatives of fatty alcohols according to the present invention are compounds of formula (III) in which D' is an acyl residue of a carboxylic acid selected from the group consisting of citric acid, sulfosuccinic acid, tartaric acid, malic acid and maleic acid.

An example of preparation of the anionic derivatives of fatty alcohols of formula (III) has been reported in the article "*Citric Ester Surfactants*"—P. J. Borchert et al.—Proceeding of the World Surfactants Congress—Munich 1984, vol. 2, pag. 147.

Particularly relevant for the realisation of the present invention are the anionic derivatives of alkylpolyglycosides (II) and the anionic derivatives of fatty alcohol (III) in which D and D' are acyl residues of citric acid with at least one carboxylic group salified, preferably in the form of sodium salt.

In the surfactant mixture useful for the realisation of the present invention, the R group in the compound of formula (I), the R' group in the compound of formula (II) and the R" group of the fatty alcohol of formula (III) can be equal or different from one another.

Similarly, in the surfactant mixture useful for the realisation of the present invention, the D group in the compound of formula (II) and the D' group in the compound of formula (III) can be equal or different from one another.

According to the present invention, particularly preferred are surfactant mixtures in which R=R'=R" and simultaneously D=D'.

Among the methyl esters of fatty acids deriving from transesterification of vegetable oils useful as component b) of the microemulsions of the present invention methyl oleate is particularly preferred.

Examples of vegetable oils which are suitable as component b) are corn oil, soya oil, rapeseed oil, sunflower oil and their mixtures.

Ethoxylated and/or propoxylated derivatives of linear or branched fatty alcohols having from 6 to 20 carbon atoms and containing an average of 4 to 20 ethylene oxide and/or propylene oxide total units are preferred as component c); ethoxylated isodecylalcohol is particularly preferred as component c).

The microemulsions according to the invention advantageously contain from 0 to 15% by weight of an antifreezing agent; suitable antifreezing agents are glycerine and glycols, such as monopropylene glycol, ethylene glycol, dipropylene glycol.

Numerous mixtures of well-known single adjuvants, mainly surfactants and transesterified vegetable oils, have been prepared to investigate their efficacy.

It was recognised that the microemulsions of the invention, although upon dilution with water they become macroemulsions (oil-in water), the phenomenon is reversible: when water evaporates, as it happens with deposited droplets are sprayed on the field, microemulsion is formed again, thus providing the foliage with a very efficacy adjuvant system assisting the penetration of the pesticide.

The micromelusions of the present invention increase the activity of a lot of foliar herbicides and systemic fungicides.

When the plants are treated, a suitable quantity of fungicide or, alternatively, commercial formulations containing said fungicide can be added to the adjuvant. These commercial formulations are generally emulsifiable liquids, wettable powders, concentrated suspensions, water emulsions or microemulsions.

The adjuvants of the present invention are conveniently added into herbicidal or fungicide formulations in quantities of between 0.05 and 0.5%, preferably between 0.1 and 0.3% by weight.

Example of utilisable formulations are formulations containing: triazolic: tetraconazole, triadimefon, triadimenol, propiconazole, diclobutrazol, biternatol, penconazole, flutriafol, hexaconazole, myclobutanyl, flusilazole cyproconazole, diniconazole, difenocaonazole, epoxiconazole; imidazolic: prochloraz, imazalil; morpholinic: fenpropimorph; tridemorph; dicarboxyimidic: iprodione, chlozolinate, vinclozolin; piperidinic: fenpropidin; acylalanicinic: metalaxyl, benalaxyl; Glyphosate; Glufosinate; MCPA; MCPP; Diclorprop; Dicamba; Bentazon; loxynil; Bromoxynil; Phenmedipham; Desmedipham; Ethofumesate; Propanil; Chlorsulfuron; Methsulfuron; Orthosulfamuron; Rimsulfuron; Nicosulfuron.

The preferred source of the active systemic fungicidal principle consists of commercial formulations which contains it and which is used in relation to the application with the minimum dosages recommended by the producer. According to a particular embodiment of the invention, concentrated fungicidal compositions ready for dilution containing one or more systemic fungicides and the adjuvant of the present invention, can also be prepared.

The availability of these formulations allows a correct dosage of the active principle and adjuvant, thus reducing the risks deriving from the handling of unexperienced operators.

In the examples the following compounds were used:

Ethoxylated Fatty Alcohol:

CoA=5 moles ethoxylated cetyl oleyl alcohol

ISD=90% by weight 7 moles ethoxylated isodecyl alcohol in water

Mixture of Surfactants (% are by Weight):

A=30% aqueous solution of: 47% $C_{10-16}$ alkylpolyglucoside (n=1.2); 45% $C_{10-16}$ alkylpolyglucoside (n=1.2) citric acid ester sodium salt; 8% $C_{10-16}$ fatty alcohol citric acid ester sodium salt.

B=45% aqueous solution of: 42% $C_{10-16}$ alkylpolyglucoside (n=1.2); 45% $C_{10-16}$ alkylpolyglucoside (n=1.2) sulfosuccinic acid ester sodium salt; 6% $C_{10-16}$ fatty alcohol sulfosuccinic acid ester sodium salt.

Methyl Ester of Vegetable Oil:

MeO=metil oleate

Antifreezing agent:

MPG=monopropylene glycol

EXAMPLES 1-8

Microemulsions according to the invention were prepared by homogenising under mechanical moderate stirring the ingredients listed in Table 1 (numbers are parts by weight).

TABLE 1

| | Ex. 1 | Ex. 2 | Ex. 3 | Ex. 4 | Ex. 5 | Ex. 6 | Ex. 7 | Ex. 8 |
|---|---|---|---|---|---|---|---|---|
| MeO | 25.5 | 31.5 | 31.5 | 30 | 31.3 | 31.5 | 31.5 | 31.5 |
| CoA | 8 | 10 | 30.0 | 30 | 31.3 | — | — | — |
| ISD | 31.5 | 31.5 | — | — | — | 31.5 | 31.2 | 31.2 |
| A | 29 | 30.5 | 33.5 | 29 | 28.1 | 31 | 28.1 | — |
| B | — | — | — | — | — | — | — | 28.1 |
| Water | 2.5 | 4 | — | — | — | — | 3.1 | 3.1 |
| MPG | 10 | 9 | 6.5 | 10 | 9.4 | 6.5 | 6.2 | 6.2 |

The microemulsions of Examples 1-8 are perfectly clear and transparent and have good storage stability: that is, they are clear homogeneous transparent liquids not only at room temperature but if kept at 10° C. and at 40° C. for 4 weeks. At high dilution rate (practical dosage rate) they form oil-in-water macro-emulsions. Same behaviour occurs when tank-mix is being prepared combining suitable formulation containing pesticide active ingredient. The microemulsions of Examples 1-8 are pourable low viscous liquids (viscosity<100 mPa·s).

Particle size determination of the microemulsion of Example 7 revealed an average particle size of 15 to 40 nm at 25° C. (instrument: N4Plus, Coulter).

The invention claimed is:

1. Microemulsions containing: a) a mixture of surfactants comprising i) one or more anionic derivatives of an alkylpolyglycoside; ii) one or more alkylpolyglycosides; iii) one or more anionic derivatives of a fatty alcohol; b) one or more methyl esters of fatty acids deriving from the transesterification of vegetable oils, one or more vegetable oils, or mixture thereof; c) one or more non ionic surfactants; d) water wherein the microemulsion contains: a) from 5 to 20% by weight of the mixture of surfactants, the mixture comprising from 30% to 60% by weight of anionic derivative of an alkylpolyglycoside, from 30% to 60% by weight of alkylpolyglycoside and from 5% to 20% by weight of anionic derivative of fatty alcohol, their balance being 100; b) from 20 to 40% by weight of methyl esters of fatty acids deriving from transesterification of vegetable oils or from 20 to 40% by weight of vegetable oils; c) from 25 to 35% by weight of non ionic surfactants; d) from 10 to 40% by weight of water.

2. Microemulsions according to claim 1, wherein c) is an ethoxylated and/or propoxylated derivative of linear or branched fatty alcohols having from 6 to 20 carbon atoms.

3. Microemulsions according to claim 2, wherein: the alkylpolyglycosides of the mixture of surfactants are the aliphatic alkylpolyglycosides represented by the formula (I) R—O-$(G)_x$ where R is a saturated or unsaturated aliphatic group having from 6 to 20 carbon atoms, linear or branched; O is an oxygen atom; G is a residue of a reducing saccharide connected to R—O by means of an ethereal O-glycosidical bond; x is a number from 1 to 10, representing the average degree of oligomerisation of G; the anionic derivatives of alkylpolyglycosides of the mixture of surfactants are compounds represented by the formula (II) $[R'—O-(G)_x]_n-(D)_y$ where R' is a aliphatic group, saturated or unsaturated, linear or branched, having from 6 to 20 atoms of carbon; G is a residue of a reducing saccharide connected to R'—O by means of an ethereal O-glycosidical bond; is an oxygen atom; D is an acyl residue connected to an oxygen atom of the residue G, and derived from a bicarboxylic acid or a polycarboxylic acid having an aliphatic chain from 2 to 8 carbon atoms, linear or branched, saturated or unsaturated, not substituted or substituted with one or more hydroxyl groups, and in which at least one carboxylic group is salified or in acid form; n is a number between 1 and m−1, where m is the number of carboxylic groups in the acid that originates O; x has the same meaning as described above for the compounds of formula (I); y is a number from 1 to 10 representing the degree of average esterification of $(G)_x$; the anionic derivatives of fatty alcohols of the mixture of surfactants are represented by the formula (III) R"—O—O' and they can be prepared by esterification of a carboxylic acid with a fatty alcohol of formula R"-OH, where R" is an aliphatic group, saturated or unsaturated, linear or branched, having from 6 to 20 atoms of carbon; O is an oxygen atom; D' is an acyl residue of a bicarboxylic acid or of a polycarboxylic acid having an aliphatic chain with from 2 to 8 atoms of carbon, saturated or unsaturated, linear or branched, not substituted or substituted with one or more hydroxyl groups, and in which at least one carboxyl group is salified or in its acid form.

4. Microemulsions according to claim 3, wherein: the alkylpolyglycosides are compounds of formula (II), in which R is an alkyl group having from 8 to 16 atoms of carbon, G is a residue of a reducing saccharide and x is a number between 1 and 2; the anionic derivatives of alkylpolyglycosides are compounds of formula (II), in which R' is an alkyl group having from 8 to 16 atoms of carbon and D is the acyl residue of a carboxylic acid selected from the group consisting of citric acid, sulfosuccinic acid, tartaric acid, maleic acid and malic acid; the anionic derivatives of fatty alcohols are compounds of formula (III) in which R" is an alkyl group having from 8 to 16 atoms of carbon and D' is an acyl residue of a carboxylic acid selected from the group consisting of citric acid, sulfosuccinic acid, tartaric acid, malic acid and maleic acid.

5. Microemulsions according to claim 4, wherein in formula (I) and (II) G is a residue of glucose.

6. Microemulsions according to claim 5, wherein component b) is methyl oleate.

7. Microemulsions according to claim 6, wherein component c) is one or more ethoxylated and/or propoxylated derivatives of linear or branched fatty alcohols having from 6 to 20 carbon atoms and containing an average of 4 to 20 ethylene oxide and/or propylene oxide total units.

8. Microemulsions according to claim 7, wherein in formula (II) and (III) D and D' are acyl residues of citric acid with at least one carboxylic group salified.

9. Microemulsions according to claim 8, wherein the R group in the compounds of formula (I), the R' group in the compounds of formula (II) and the R" group of the compounds of formula (III) are equal.

10. Microemulsions according to claim 9, wherein component c) is ethoxylated isodecylalcohol.

11. Herbicidal or fungicide formulations comprising from 0.05 to 0.5% by weight of a microemulsion according to claim 1.

12. Herbicidal or fungicide formulations comprising from 0.05 to 0.5% by weight of a microemulsion according to claim 2.

13. Herbicidal or fungicide formulations comprising from 0.05 to 0.5% by weight of a microemulsion according to claim 3.

14. Herbicidal or fungicide formulations comprising from 0.05 to 0.5% by weight of a microemulsion according to claim 4.

15. Herbicidal or fungicide formulations comprising from 0.05 to 0.5% by weight of a microemulsion according to claim 5.

16. Herbicidal or fungicide formulations comprising from 0.05 to 0.5% by weight of a microemulsion according to claim 6.

17. Herbicidal or fungicide formulations comprising from 0.05 to 0.5% by weight of a microemulsion according to claim 7.

18. Herbicidal or fungicide formulations comprising from 0.05 to 0.5% by weight of a microemulsion according to claim 8.

19. Herbicidal or fungicide formulations comprising from 0.05 to 0.5% by weight of a microemulsion according to claim 9.

20. Herbicidal or fungicide formulations comprising from 0.05 to 0.5% by weight of a microemulsion according to claim 10.

* * * * *